United States Patent
Nagasaka

(10) Patent No.: US 8,432,162 B2
(45) Date of Patent: Apr. 30, 2013

(54) MAGNETIC SENSOR USING AN OPTICAL PUMPING METHOD

(75) Inventor: Kimio Nagasaka, Hokuto (JP)

(73) Assignee: Seiko Epson Corporation, Tokyo (JP)

( * ) Notice: Subject to any disclaimer, the term of this patent is extended or adjusted under 35 U.S.C. 154(b) by 505 days.

(21) Appl. No.: 12/759,905

(22) Filed: Apr. 14, 2010

(65) Prior Publication Data

US 2010/0327862 A1 Dec. 30, 2010

(30) Foreign Application Priority Data

Jun. 24, 2009 (JP) ................................. 2009-150032

(51) Int. Cl.
*G01R 33/032* (2006.01)
(52) U.S. Cl.
USPC ...................................................... 324/244.1
(58) Field of Classification Search .............. 324/244.1
See application file for complete search history.

(56) References Cited

U.S. PATENT DOCUMENTS

| | | | | |
|---|---|---|---|---|
| 6,822,737 B2 * | 11/2004 | Kurata et al. | ............... | 356/364 |
| 2006/0176542 A1 * | 8/2006 | Muro et al. | ............... | 359/290 |

OTHER PUBLICATIONS

Yabuzaki, "Atomic physics with laser beam," *Iwanami Shoten*, 2007, pp. 29-57 (with translation).
Kitano et al., "Symmetry-recovering crises of chaos in polarization-related optical bistability," *Physical Review A*, Mar. 1984, pp. 1288-1296, vol. 29, No. 3, The American Physical Society.

* cited by examiner

*Primary Examiner* — Jay Patidar
(74) *Attorney, Agent, or Firm* — Oliff & Berridge, PLC

(57) ABSTRACT

A magnetic sensor that measures a magnetic field by using an optical pumping method, the magnetic sensor including: a cell that encloses therewithin atoms or ions each having a single electron in the outermost shell thereof and that is arranged inside the magnetic field; a light source that causes pulsed first linearly polarized light to be incident upon the cell; a circularly polarized light generator that converts a portion of second linearly polarized light, which is the first linearly polarized light having passed through the cell, into elliptically or circularly polarized light and causes the portion of second linearly polarized light to be incident upon the cell; and a polarimeter that detects an angle of rotation of a first polarization plane, which is polarization plane of the first linearly polarized light, and an angle of rotation of a second polarization plane, which is a polarization plane of the second linearly polarized light.

6 Claims, 5 Drawing Sheets

Prior Art

MAGNETIC SENSOR USING AN OPTICAL PUMPING METHOD

BACKGROUND

1. Technical Field

The present invention relates to magnetic sensors and the like that measure minute magnetic fields generated by for example living bodies such as cardiac magnetic fields and neural magnetic fields by using an optical pumping method.

2. Related Art

The use of magnetic sensors that utilize optically pumped atomic magnetometers as a method of measuring minute magnetic fields has been considered. In such a method, a magnetic field is measured by optically pumping atoms of a gas and then detecting the magnetization of the atoms through the interactions between the atoms and the magnetic field. With such a method, there is no need to employ a large cooling mechanism as is necessary in the case of using superconducting quantum interference devices (SQUIDS) for example and the structure of the measurement device can be simplified and the cost can be reduced (For example refer to Reezaakou ni yoru genshibutsuri, Tsutomu Yabuzaki, Iwanami Shoten (2007), p. 29-57 and "Symmetry-recovering crises of chaos in polarization-related optical bistability", M. Kitano, T. Yabuzaki, and T. Ogawa, Phys. Rev. A 29, 1288-1296 (1984)).

The basic structure of an optically pumped atomic magnetometer is illustrated in FIG. 7. In FIG. 7, a gas cell 103 is arranged between transparent heaters 101 and 102 composed of ITO or the like and laser light 105 is transmitted through these components. A gas (vapor) of alkali metal atoms such as cesium, rubidium or potassium atoms and a buffer gas such as helium, argon or nitrogen are enclosed within the gas cell 103 in suitable amounts. A magnetic field $B_O$ is a target of measurement and extends in a direction that is orthogonal to the direction in which the laser light 105 propagates. The amount of laser light 105 that is transmitted through the components is detected by a photodetector 104.

When $B_O$=0, the alkali metal atoms absorb the circularly polarized laser light 105 and are thereby optical pumped, and the number N+ (population) of atoms possessing a magnetic moment that is parallel to the direction of propagation of the laser light 105 becomes larger than the number of atoms N– possessing a magnetic moment that is antiparallel to the direction of propagation of the laser light 105 and the gas enters a so-called spin polarized state. When N+ reaches a saturation level; due to repeated optical pumping, the atoms no longer readily absorb the laser light 105 (pumping light) and the proportion of light transmitted through the components becomes large. On the other hand, when $B_O$ has a finite value, since the magnetic moments of the atoms undergo Larmor precession about an axis parallel to the direction of $B_O$, the difference between N+ and N– become substantially small. As a result, the atoms come to readily absorb the laser light 105 and the proportion of light transmitted through the components is reduced.

However, the magnetic fields generated by living bodies such as cardiac magnetic fields and neural magnetic fields are very weak, for example on the order of 100 pT, and so separating and detecting only the signal corresponding to the magnetic field of the living body from among for example noise generated by the output laser light 105 and electrical noise generated by the photodetector 104 and stages subsequent thereto is very difficult.

SUMMARY

An advantage of some aspects of the invention is that it provides a magnetic sensor that is capable of detecting a minute magnetic field with high sensitivity.

According to a first aspect of the invention, a magnetic sensor that measures a magnetic field by using an optical pumping method, includes: a cell that encloses therewithin atoms or ions each having a single electron in the outermost shell thereof and that is arranged inside the magnetic field; a light source that causes pulsed first linearly polarized light to be incident upon the cell; a circularly polarized light generator that converts a portion of second linearly polarized light, which is the first linearly polarized light having passed through the cell, into elliptically or circularly polarized light and that causes the portion of second linearly polarized light to be incident upon the cell; and a polarimeter that detects an angle of rotation of a first polarization plane, which is polarization plane of the first linearly polarized light, and an angle of rotation of a second polarization plane, which is a polarization plane of the second linearly polarized light.

With the magnetic sensor according to the first aspect of the invention, first, in a state in which elliptically polarized light or circularly polarized light is not incident upon the cell, the atoms or ions within the cell are slightly magnetized (spin polarized) by the magnetic field and possess a minute initial magnetization. In such a state, when first linearly polarized light is incident upon the cell, the polarization plane of the first linearly polarized light is slightly rotated due to the Faraday effect caused by the initial magnetization. The angle of rotation of the polarization plane (angle of Faraday rotation) is very small, but when elliptically polarized light or circularly polarized light is made incident upon the cell by the circularly polarized light generator, the atoms or ions absorb the elliptically polarized light or circularly polarized light, spin polarization (magnetization) is generated and the angle of Faraday rotation is increased.

Here, when elliptically polarized light or circularly polarized light is continuously incident on the inside of the cell, the magnetization of the atoms or ions increases in the form of an exponential function and before long converges with a saturation level. The rate of increase of the magnetization differs depending on the initial magnetization and therefore the size of the initial magnetization, that is, the magnitude of the magnetic field, can be measured by measuring this rate of increase.

At this time, when the intensity of the elliptically polarized light or circularly polarized light continuously incident on the inside of the cell is constant, the magnetization of the atoms or ions rapidly reaches the saturation level and therefore with the magnetic sensor according to the first aspect of the invention a portion of the first linearly polarized light emitted in pulses is converted into elliptically polarized light or circularly polarized light and this light is made incident upon the cell. With the magnetic sensor, the magnetization of the atoms or ions is gradually amplified by the elliptically polarized light or circularly polarized light intermittently incident on the cell, and therefore the change with time of the magnetization (dynamic behavior) can be accurately measured. Accordingly, by applying a predetermined theoretical equation to analyze the change of the magnetization with time, the size of the initial magnetization, that is, the magnitude of the magnetic field can be correctly obtained without performing amplification with an electrical circuit.

In the magnetic sensor according to the first aspect of the invention, the circularly polarized light generator preferably causes elliptically polarized light or circularly polarized light, whose intensity varies periodically, to be incident upon the cell, and when a maximum light intensity of the elliptically polarized light or circularly polarized light incident upon the cell from the circularly polarized light generator is denoted by $I_{max}$, a minimum light intensity of the elliptically polarized light or circularly polarized light incident upon the cell from the circularly polarized light generator is denoted by $I_{min}$, and a minimum light intensity of the elliptically polarized light or circularly polarized light that can cause spin polarization of the atoms or the ions enclosed in the cell when the magnetic field is zero is denoted by $I_C$, the relation between $I_C$, $I_{max}$ and $I_{min}$ of $I_{max} > I_C > I_{min}$ preferably holds true.

With this magnetic sensor, when the light intensity $I_O$ of the elliptically polarized light or circularly polarized light incident on the cell is made to be larger than $I_C$, the magnetization of the atoms or ions can be increased in the form of an exponential function, and when the light intensity $I_O$ of the elliptically polarized light or circularly polarized light incident on the cell is made to be smaller than $I_C$, the magnetization of the atoms or ions can be allowed to return to the initial magnetization. Then, by adjusting the time over which the magnetization of the atoms or ions is caused to increase and the time over which the magnetization of the atoms and ions is allowed to return to the initial magnetization, the dynamic behavior (change with time) of the magnetization is more easily controlled and thus accurate measurement of the initial magnetization can be made.

This magnetic sensor preferably further includes a calculation device that samples and holds an output of the polarimeter at a timing that matches the period of the pulsed second linearly polarized light and calculates the magnitude of the magnetic field on the basis of the change with time of the sampled and held output.

With this magnetic sensor, the error due to calculation can be made small and thus accurate measurement of the magnetic field can be made.

In the magnetic sensor according to the first aspect of the invention, it is preferable that the circularly polarized light generator be arranged on the optical path of the second linearly polarized light, which has passed through the cell, and include an ⅛ wave plate that creates a phase difference of ⅛ wavelength in the second linearly polarized light and a first reflective plate that reflects light, which is the second linearly polarized light having passed through the ⅛ wave plate, and makes the light be incident upon the ⅛ wave plate and the cell.

With this magnetic sensor, pulsed elliptically polarized light or circularly polarized light can be easily made incident on the cell by using a simple structure.

In this magnetic sensor, it is preferable that the first reflective plate allow a portion of the light that has passed through the ⅛ wave plate to pass therethrough and make the portion of light be incident upon the polarimeter.

With this magnetic sensor, the angles of rotation of the polarization planes of the first linearly polarized light and the second polarized light can be easily measured by using a simple structure.

In this magnetic sensor, the circularly polarized light generator preferably further includes a second reflective plate that is arranged on an optical path of light that has been reflected by the first reflective plate and has passed through the ⅛ wave plate and the cell, and the first reflective plate and the second reflective plate preferably form an optical resonator that causes the light to resonate.

With this magnetic sensor, the speed with which a process of amplifying the magnetization is performed can be increased. Consequently, the change of magnetization with time can be measured in more detail and therefore accurate measurement of the magnetic field can be made.

In this magnetic sensor, it is preferable that the second reflective plate be arranged on the optical path of the first linearly polarized light incident on the cell from the light source and allow a portion of the first polarized light to pass therethrough and be incident upon the cell and it is preferable that the second reflective plate reflect a portion of the light reflected by the first reflective plate and having passed through the ⅛ wave plate and the cell and make the portion of the light be incident upon the cell.

With this magnetic sensor, an optical resonator structure can be easily realized by using a simple structure.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Figure 1:
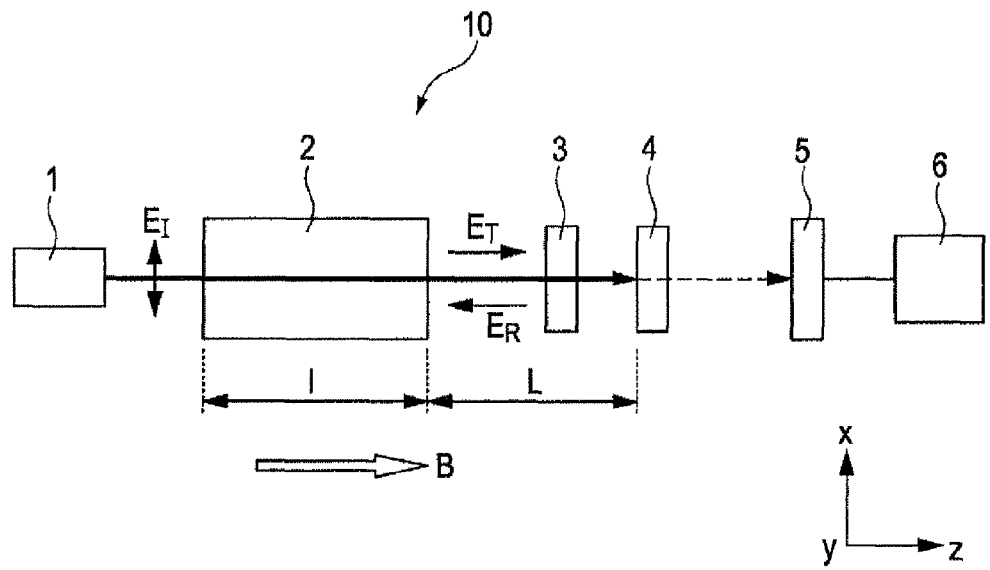
FIG. 1 is an outline view of the structure of a magnetic sensor according to a first embodiment.

FIG. 1 is an outline view of the structure of a magnetic sensor 10 according to a first embodiment of the invention. The magnetic sensor 10 uses an optical pumping method and includes a light source 1, a cell 2, an ⅛ wave plate 3, a first reflective plate 4, a polarimeter 5 and an calculation device 6. In the following description, an xyz Cartesian coordinate system will be used, taking the direction of an external magnetic field B as the z axis and two directions that lie in the same plane and are orthogonal to the z axis as the x and y axes. The structure and position of each component will be explained.

The light source 1 is a laser light source that emits first linearly polarized light $E_I$. The light source 1 makes pulses of the light $E_I$ be incident upon the cell 2 in a direction that is parallel to the direction of the external magnetic field B. It is preferable that the light $E_I$ emitted from the light source 1 be substantially composed of only linearly polarized light, but so long as the light $E_I$ contains a component of linearly polarized light the light $E_I$ may contain components having other polarizations.

A gas (vapor) of alkali metal atoms such as cesium, rubidium or potassium atoms is enclosed within the cell 2. In this embodiment, atoms (alkali metal atoms) each having a single electron in the outermost shell thereof are enclosed in the cell 2, but a similar effect can be obtained when ions each having a single electron in the outermost shell thereof are enclosed in the cell 2. A buffer gas such as helium, argon or nitrogen may also be enclosed in the cell 2, in addition to the gas of alkali metal atoms. The buffer gas suppresses the occurrence of collisions between the alkali metal atoms and suppresses the occurrence of collisions between the alkali metal atoms and the inner wall of the cell 2. Any material that allows the light $E_I$ emitted from the light source 1 to pass therethrough can be used as the material of the cell 2 and a transparent material such as a glass or plastic can be used.

The ⅛ wave plate 3 and the first reflective plate 4 form a circularly polarized light generator that converts a portion of second linearly polarized light $E_T$, which is the first linearly polarized light having passed through the cell 2, into elliptically polarized light or circularly polarized light $E_R$ and makes the elliptically polarized light or circularly polarized light $E_R$ be incident upon the cell 2. The ⅛ wave plate 3 is formed from a crystal exhibiting birefringence and, when the two main optical axes are taken to be the x axis and the y axis, creates a phase difference of 45° (⅛ of the wavelength) between waves oscillating along the x axis and the y axis.

Having passed through the cell 2, the second linearly polarized light $E_T$ passes through the ⅛ wave plate 3 and is incident upon the first reflective plate 4; then, a portion of the light passes through the first reflective plate 4 and is incident upon the polarimeter 5. The remaining portion of the light is reflected by the first reflective plate 4 and is made re-incident upon the ⅛ wave plate 3. The second linearly polarized light $E_T$, which has passed through the cell 2, is pulsed linearly polarized light whose incident light intensity increases and decreases in a cycle with a predetermined period, and therefore the light $E_R$ that is re-incident upon the cell 2 from the ⅛ wave plate 3 (in other words the light $E_R$ emitted from the circularly polarized light generator to the cell 2) is also pulsed light whose incident light intensity increases and decreases in a cycle with a predetermined period.

Since the light $E_R$ passes through the ⅛ wave plate 3 two times, the aforementioned phase difference between the two waves having orthogonal polarizations is 90° (¼ the wavelength). If the polarization of the light $E_T$ incident upon the ⅛ wave plate 3 is in the direction of the x axis, the change in polarization is small, but if the polarization is inclined at even a small angle relative to the x axis, the light $E_R$ that is returning to the cell 2 becomes elliptically polarized.

Elliptically polarized light can be expressed as a sum of left-handed circularly polarized light and right-handed circularly polarized light having different amplitudes and possesses angular momentum. Therefore, when atoms within the cell 2 absorb this elliptically polarized light and are optically pumped, the atoms becomes spin polarized. Strictly speaking, the ⅛ wave plate 3 and the first reflective plate 4 convert a portion of the light $E_T$, which has passed through the cell 2, into elliptically polarized light or circularly polarized light and make the light be incident upon the cell 2 and since elliptically polarized light also causes optical pumping in the same way as circularly polarized light, in the present specification, sometimes both circularly polarized light and elliptically polarized light are expressed as circularly polarized light without differentiating between the two.

In the magnetic sensor 10 having the above-described configuration, when the cell 2 is not subject to laser irradiation, the alkali metal atoms enclosed within the interior of the cell 2 are slightly magnetized (spin polarized) by the external magnetic field B. The initial value of this magnetization (initial magnetization) is denoted by $M_i$.

Here, a linearly polarized light beam $E_I$ that propagates along the x axis is output from the light source 1 and passes through the cell 2. The intensity of the light $E_I$, which is incident upon the cell 2, is denoted by $I_O$. The plane of polarization of the light $E_T$, which has passed through the cell 2, is slightly rotated due to the Faraday effect caused by the initial magnetization $M_i$, and a y-axis component is created. Subsequently, after passing through the ⅛ wave plate 3 and being reflected by the first reflective plate 4, the light passes once again through the ⅛ wave plate 3. Through this process, a phase difference of π/2 (¼ of the wavelength) is generated between the x-axis component and the y-axis component, the light becomes the elliptically polarized light $E_R$ and is incident once again on the cell 2.

Since elliptically polarized light can be expressed as the sum of left-handed circularly polarized light and right-handed circularly polarized light having different amplitudes, if the alkali metal atoms inside the cell 2 absorb the elliptically polarized light $E_R$, spin polarization is promoted and the angle of Faraday rotation becomes large. So-called positive feedback of spin polarization (angle of Faraday rotation) occurs. However, the initial magnetization $M_i$ eventually converges to the saturation magnetization $M_O$. Spin polarization can be detected by measuring the angles of rotation of the polarization planes of light $E_I$ and light $E_T$ before and after passing through the cell 2 with the polarimeter 5. The calculation device 6 detects the magnitude of the external magnetic field B on the basis of the angles of rotation of the polarization planes detected by the polarimeter 5.

Figure 2:
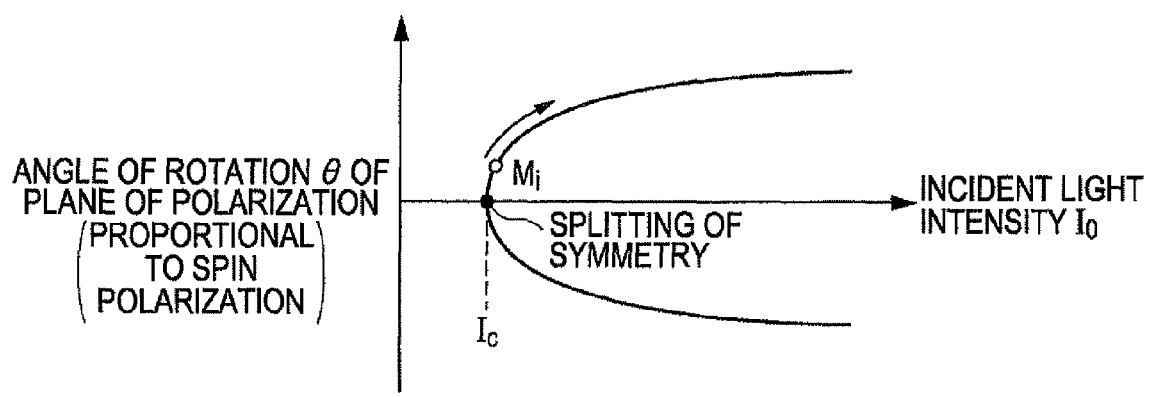
FIG. 2 is a plot illustrating the dependency of spin polarization on light intensity.

The relationship between the incident light intensity $I_O$ and spin polarization is illustrated in FIG. 2. For an external magnetic field B of zero, when the incident light intensity $I_O$ is small, the individual spins of the alkali metal atoms inside the cell 2 are oriented in random directions and there is no overall spin polarization. In contrast, when the incident light intensity $I_O$ is increased and reaches a certain predetermined critical value $I_C$, symmetry splitting occurs and spin polarization occurs.

In the case where the polarization direction of the light $E_T$ exactly matches the direction of the x axis of the ⅛ wave plate 3 and there is total symmetry between left-handedness and right-handedness, which of the two polarities of spin polarization occurs is random, whereas in the case where there is an external magnetic field B and the initial magnetization $M_i$ has a finite value, the polarity of the initial polarization $M_i$ determines the polarity of the final spin polarization.

Here, the dynamic behavior of the spin polarization in the case in which the incident light intensity $I_O$ is larger than the critical value $I_C$ will be considered. Magnetization M(t) will be introduced as an indicator of spin polarization. For details of how magnetization M(t) was derived, refer to "Symmetry-recovering crises of chaos in polarization-related optical bistability", M. Kitano, T. Yabuzaki, and T. Ogawa, Phys. Rev. A 29, 1288-1296 (1984).

Similarly to as in the previous process, if the magnetization at the time when the incident light intensity $I_O$ is zero (initial magnetization) is denoted by $M_i$, the saturation magnetization is denoted by $M_O$ and it is assumed that M(t) is much less than $M_O$, the magnetization M(t) that exists t seconds after light $E_R$ begins to be incident on the cell 2 can be obtained from the following equation.

$$M(t) = M_i e^{\alpha t} \qquad (1)$$

Here, α is a constant determined by for example the incident light intensity $I_O$, the magnetization relaxation time, the reflectivity of the first reflective plate 4 and the length W of the cell 2. According to Eq. 1, the magnetization M(t) increases as an exponential function with time t. Accordingly, the reason why the initial magnetization $M_i$ is amplified in the optical system illustrated in FIG. 1 can be understood.

Therefore, amplifying of a minute magnetic field in this way will be considered. If light $E_R$ having a fixed incident light intensity $I_O$ is continuously incident upon the cell 2, the spin polarization becomes rapidly biased to either of the polarities and therefore it is considered that the incident light intensity $I_O$ is modulated and returns to being lower than the critical value $I_O$, that is, the magnetization returns to the initial magnetization $M_i$, every period. The behavior of the incident light intensity $I_O(t)$ and the magnetization $M(t)$ at this time is illustrated in FIGS. 3A and 3B.

Figure 3A:
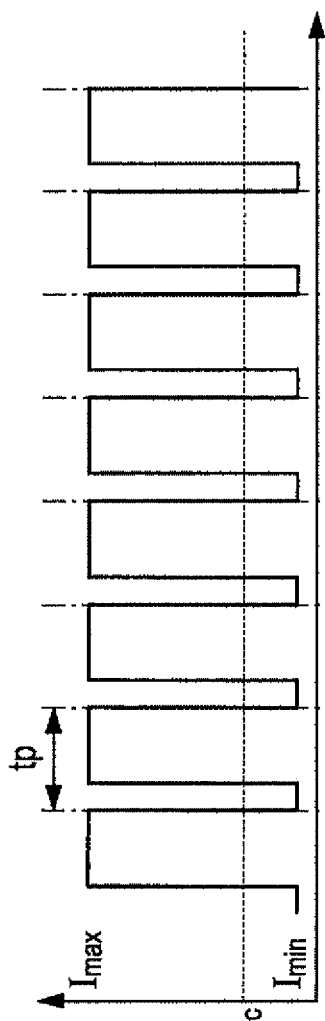
FIG. 3A is a plot illustrating the change with time of light intensity and FIG. 3B is a plot illustrating the change with time of magnetization.

In FIG. 3A, the light F is incident upon the cell 2 in the form of pulsed light having an incident light intensity $I_O$ that repeatedly increases and decreases in a cycle with a fixed period $t_p$ along the time axis. The maximum value $I_{max}$ of the incident light intensity $I_O$ is larger than the critical value $I_C$ and the minimum value $I_{min}$ of the incident light intensity $I_O$ is smaller than the critical value $I_C$.

Figure 3B:
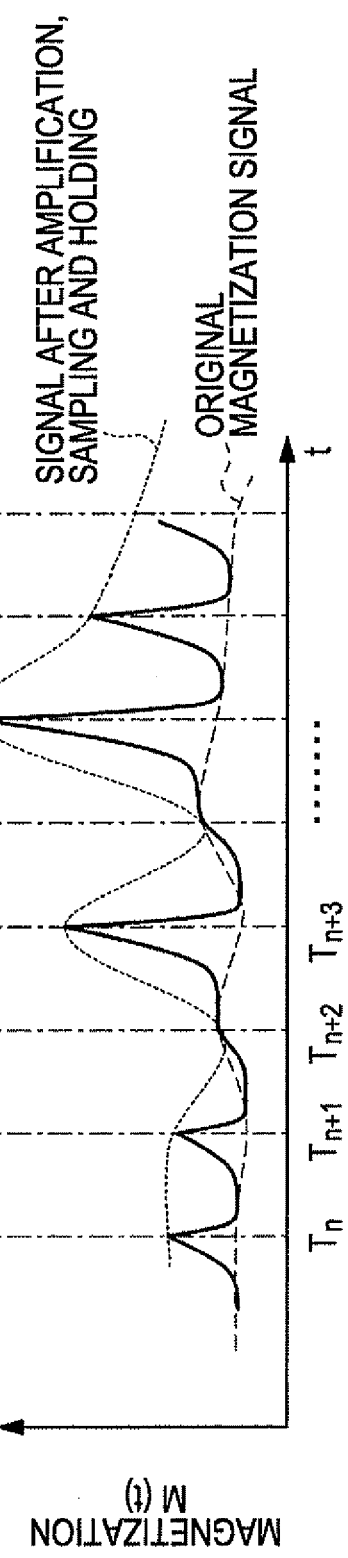

As illustrated in FIG. 3B, when the incident light intensity $I_O$ is made to be larger than the critical value $I_C$, the magnetization begins to experience positive feedback and increases as an exponential function. When the incident light intensity $I_O$ is made to be smaller than the critical value $I_C$ after a predetermined period of time has elapsed (the positions of such times being indicated by $T_i$ (i=n, n+1, n+2, n+3 ...)), the positive feedback stops, a relaxation time elapses, and the magnetization $M(t)$ returns to the initial magnetization. If the output of the polarimeter 5 is sampled and held at the times $T_i$, an amplified magnetization signal can be obtained. The calculation device 6 calculates the magnitude of the external magnetic field B on the basis of the change with time of the sampled and held output.

FIG. 3B is a plot illustrating the results of a simulation performed on the basis of the below theoretical equation described in "Symmetry-recovering crises of chaos in polarization-related optical bistability", M. Kitano, T. Yabuzaki, and T. Ogawa, Phys. Rev. A 29, 1288-1296 (1984).

$$\frac{dm_z(t)}{dt} = -(\Gamma + 2I_0)m_z(t) + 2RI_0\sin[2\kappa lm_z(t-t_R)] \quad (2)$$

In FIG. 3B, the change of magnetization with time is obtained by solving a differential equation for the z direction magnetization $m_z(t)$ by numerical calculation on the basis of Eq. 2. The initial magnetization $m_z(0)$ was given three values of 1.0E-5, 2.0E-5, and 4.0E-5 and the values of the constants used in the calculation are given in Table 1.

TABLE 1

| Parameter | Symbol | Value | Units |
|---|---|---|---|
| Relaxation speed | $\Gamma$ | 40 | $s^{-1}$ |
| Incident light intensity | $I_o$ | 0.014 | W |
| Mirror reflectivity | R | 0.99 | |
| | $\kappa$ | 100000 | |
| Cell length | l | 0.01 | m |
| | $t_R$ | 6.67128E−11 | s |
| Distance from end of cell to mirror | L | 0.01 | m |
| Speed of light | c | 299792458 | m/s |
| Time interval | dt | 0.001 | s |

Figure 4:
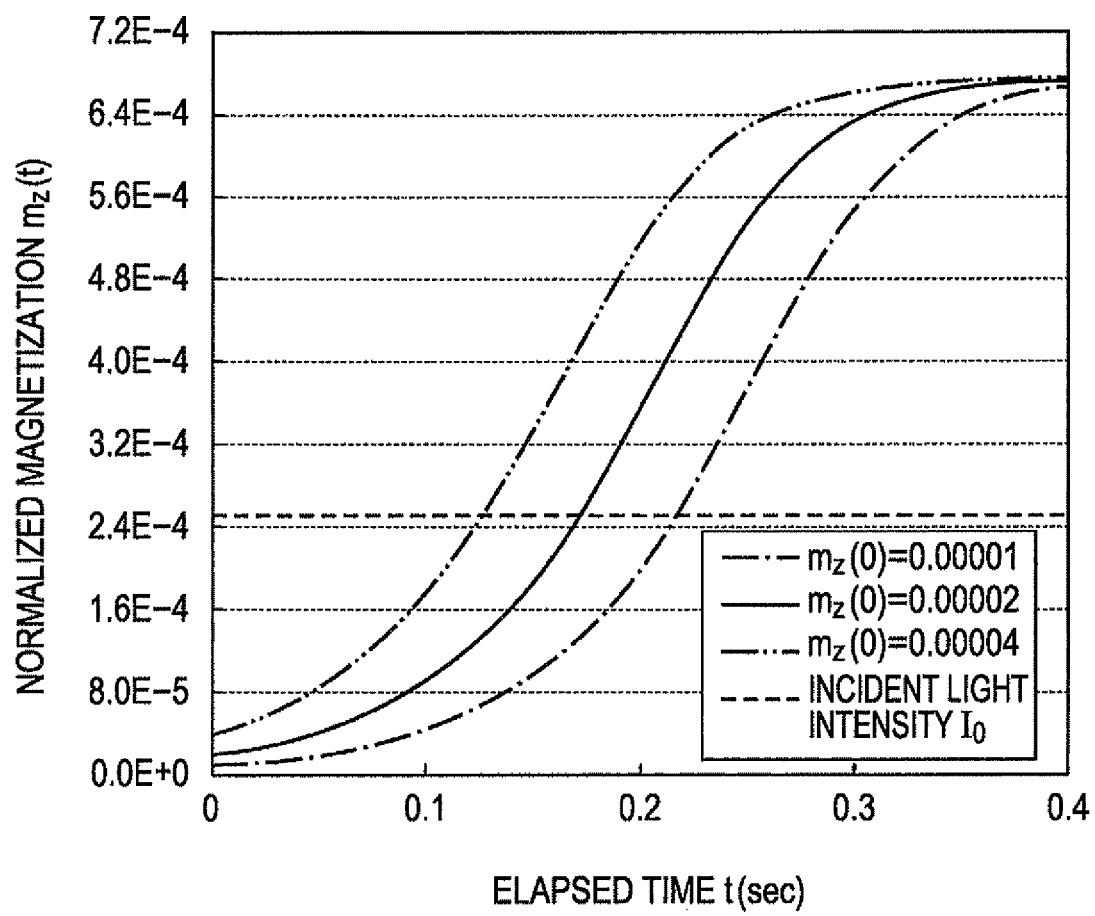
FIG. 4 is a plot illustrating the change with time of magnetization in the case of a constant light intensity.

For example, the results for the case where the cell 2 is continuously irradiated with light having an incident light intensity of 0.014 W are illustrated in FIG. 4. Initially, the magnetizations increase as exponential functions at different rates of increase depending on the initial values. However, as time elapses the magnetizations go on to converge with a saturation level.

Figure 5:
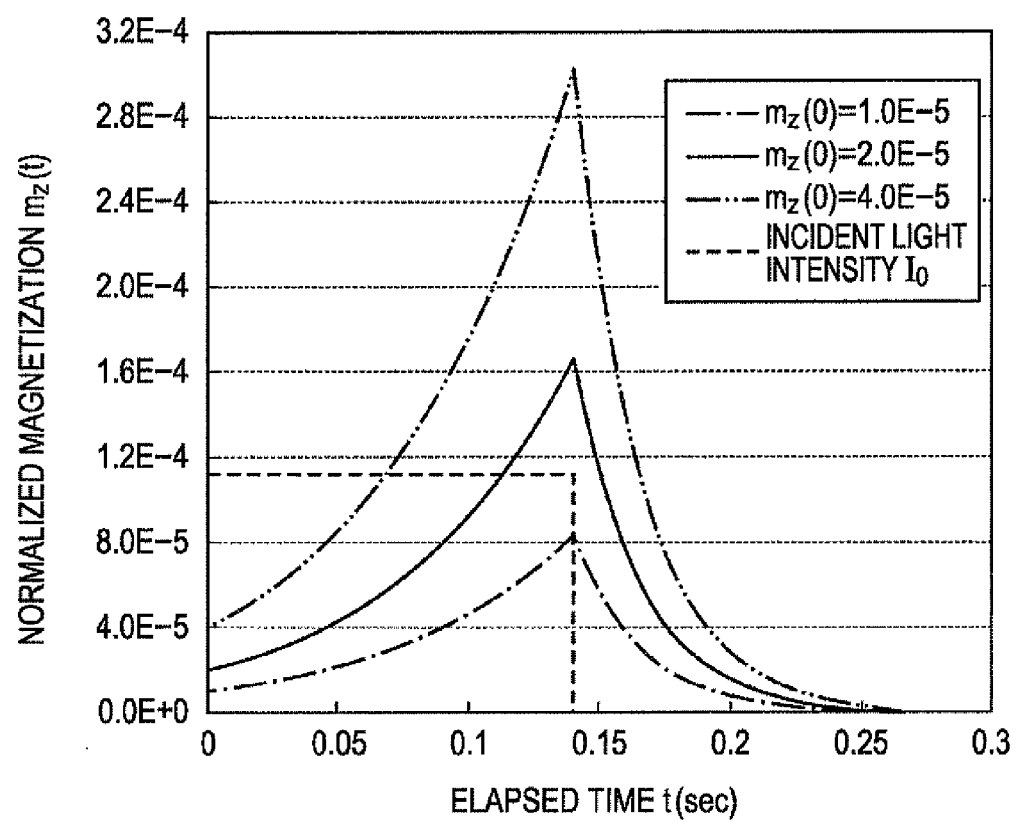
FIG. 5 is a plot illustrating the change with time of magnetization when pulsed circularly polarized light is incident upon the cell.

Next, the results obtained in the case in which the magnetization suddenly stops increasing after an irradiation time of 0.14 s has elapsed (for example a case in which the incident light intensity is made to be zero) is illustrated in FIG. 5. Amplification of the magnetization stops immediately when irradiation of the light is stopped and the magnetization begins to relax. The magnetization approximately decreases as an exponential function while relaxing. The value of the peak of the curve is approximately proportional to the initial magnetization $m_z(0)$. However, in the case where the initial magnetization $m_z(0)$ is 4.0E-5, since the magnetization is close to saturation, there is an error in the proportionality due the effect of this.

As illustrated in FIG. 3, changes in the magnetic field being measured with time can be measured by periodically emitting pulsed light. The peak of the amplified magnetization occurs at a level that reflects the initial magnetization, and a minute magnetic field can be measured with high sensitivity by detecting this peak.

Second Embodiment

Figure 6:
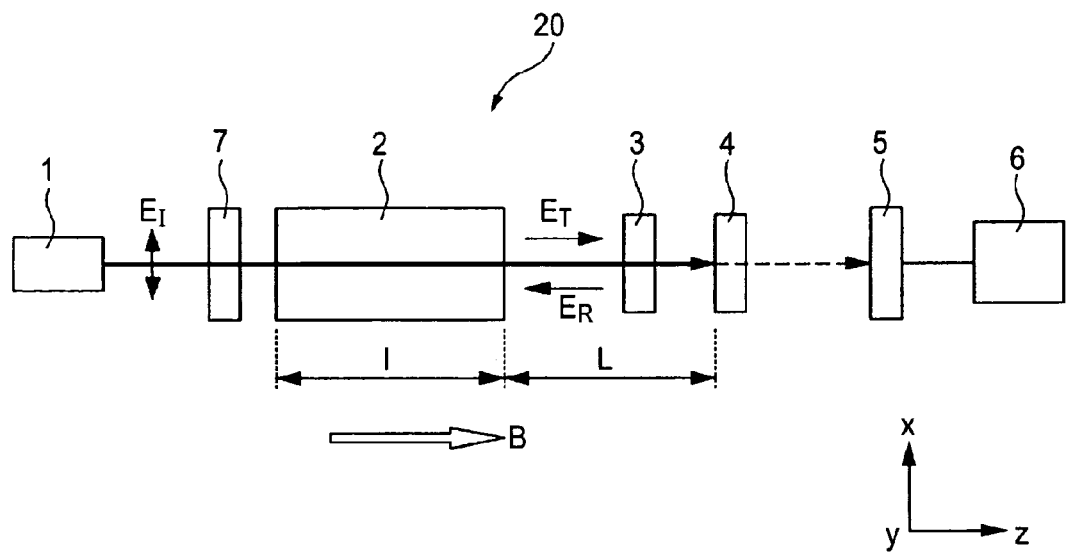
FIG. 6 is an outline view of the structure of a magnetic sensor according to a second embodiment.
Figure 7:
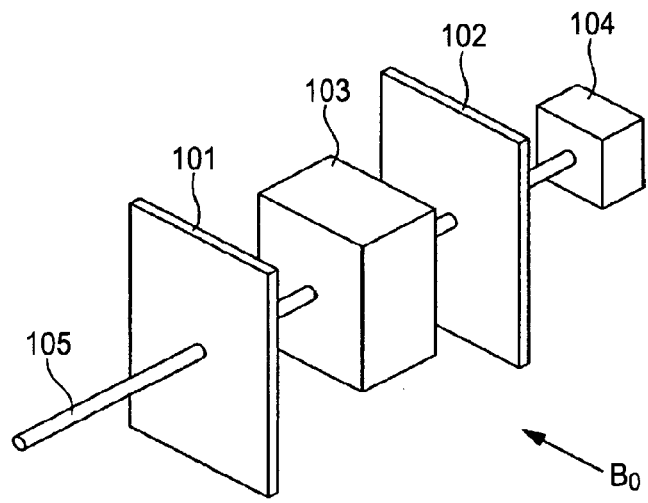
FIG. 7 is an outline view of the structure of a magnetic sensor of the related art.

FIG. 6 is a view illustrating an outline configuration of a magnetic sensor 20 according to a second embodiment of the invention. The magnetic sensor 20 according to this embodiment differs from the magnetic sensor 10 according to the first embodiment in that a second reflective plate 7 is arranged between the light source 1 and the cell 2 such that circularly polarized light is made to pass through the cell 2 a plurality of times. Therefore, components that are common to both the magnetic sensor 20 of this embodiment and the magnetic sensor 10 of the first embodiment are denoted by the same reference numerals and detailed description thereof is omitted.

The second reflective plate 7 is arranged on the optical path of the light $E_R$, which has been reflected by the first reflective plate 4 and has passed through the ⅛ wave plate 3 and the cell 2. An optical length (l, L etc.), that is, the distance between the first reflective plate 4 and the second reflective plate 7 is set such that a resonator is formed by the first reflective 4 and the second reflective plate 7.

In FIG. 6, the second reflective plate 7 is arranged on the optical path of the light $E_I$ that is incident upon the cell 2 from the light source 1. The second reflective plate 7 is configured so as to allow a portion of the light $E_I$ to pass therethrough and be incident upon the cell 2 and so as to reflect a portion of the light $E_R$, which has been reflected by the first reflective plate 4 and has passed through the ⅛ wave plate 3 and the cell 2, and make the portion of the light $E_R$ be incident upon the cell 2.

The process of amplifying the magnetization in the magnetic sensor 20 is the same as that described using FIGS. 2 to 5, except that since in the magnetic sensor 20 amplification of the magnetization is performed at a high speed due the light being made to reciprocate between the first reflective plate 4 and the second reflective plate 7, the pulse period $t_p$ illustrated in FIG. 3 can be shortened. Consequently, the temporal resolution is increased when measuring the change with time of magnetization and measurements of the magnetization can be made with higher precision.

What is claimed is:

1. A magnetic sensor that measures a magnetic field by using an optical pumping method, comprising:
   a cell that encloses therewithin atoms or ions each having a single electron in the outermost shell thereof and that is arranged inside the magnetic field;
   a light source that causes pulsed first linearly polarized light to be incident upon the cell;
   a circularly polarized light generator that converts a portion of second linearly polarized light, which is the first linearly polarized light having passed through the cell, into elliptically or circularly polarized light and causes the portion of second linearly polarized light to be incident upon the cell; and
   a polarimeter that detects an angle of rotation of a first polarization plane, which is polarization plane of the first linearly polarized light, and an angle of rotation of a second polarization plane, which is a polarization plane of the second linearly polarized light,
   the circularly polarized light generator causing elliptically polarized light or circularly polarized light, whose light intensity varies periodically, to be incident upon the cell, and when a maximum light intensity of the elliptically polarized light or circularly polarized light incident upon the cell from the circularly polarized light generator is denoted by Imax, a minimum light intensity of the elliptically polarized light or circularly polarized light incident upon the cell from the circularly polarized light generator is denoted by Imin, and a minimum light intensity of the elliptically polarized light or circularly polarized light that causes spin polarization of the atoms or the ions enclosed in the cell when the magnetic field is zero is denoted by IC, the relation between IC, Imax and Imin of Imax>IC>Imin holds true.

2. The magnetic sensor according to claim 1, further comprising:
   a calculation device that samples and holds an output of the polarimeter at a timing that matches a period of the pulsed second linearly polarized light and calculates the magnitude of the magnetic field on the basis of the change with time of the sampled and held output.

3. The magnetic sensor according to claim 1,
   wherein the circularly polarized light generator is arranged on the optical path of the second linearly polarized light, which has passed through the cell, and includes an ⅛ wave plate that creates a phase difference of ⅛ wavelength in the second linearly polarized light and a first reflective plate that reflects light, which is the second linearly polarized light having passed through the ⅛ wave plate, and makes the light be incident upon the ⅛ wave plate and the cell.

4. The magnetic sensor according to claim 3,
   wherein the first reflective plate allows a portion of the light that has passed through the ⅛ wave plate to pass therethrough and makes the portion of light be incident upon the polarimeter.

5. The magnetic sensor according to claim 4,
   wherein the circularly polarized light generator further includes a second reflective plate that is arranged on an optical path of the light that has been reflected by the first reflective plate and has passed through the ⅛ wave plate and the cell and the first reflective plate and the second reflective plate form an optical resonator that causes the light to resonate.

6. The magnetic sensor according to claim 4,
   wherein the second reflective plate is arranged on the optical path of the first linearly polarized light incident on the cell from the light source and allows a portion of the first polarized light to pass therethrough and be incident upon the cell and the second reflective plate reflects a portion of the light reflected by the first reflective plate and having passed through the ⅛ wave plate and the cell and makes the portion of the light be incident upon the cell.

* * * * *